United States Patent [19]

Kondo et al.

[11] 4,443,614

[45] * Apr. 17, 1984

[54] TRIARYLMETHANE DERIVATIVES

[75] Inventors: Mitsuru Kondo, Kawanishi; Kiyoshi Yasui, Motomachi; Makoto Miyake, Hyogo; Hiroshi Iwasaki, Kawanishi; Tetsuo Shiraishi, Hyogo, all of Japan

[73] Assignee: Kanzaki Paper Manufacturing Co., Ltd., Tokyo, Japan

[*] Notice: The portion of the term of this patent subsequent to Mar. 27, 2001 has been disclaimed.

[21] Appl. No.: 162,659

[22] Filed: Jun. 24, 1980

Related U.S. Application Data

[60] Continuation of Ser. No. 774,613, Mar. 4, 1977, which is a division of Ser. No. 699,584, Jun. 24, 1976, Pat. No. 4,045,458.

[30] Foreign Application Priority Data

Jul. 3, 1975 [JP] Japan ................................. 50-82898

[51] Int. Cl.$^3$ ............................................. C07D 209/04
[52] U.S. Cl. .................................. 548/469; 548/484; 548/485; 548/483
[58] Field of Search ................... 260/326.13; 548/469, 548/483, 484, 485

[56] References Cited

U.S. PATENT DOCUMENTS

4,045,458  8/1977  Kondo et al. .................... 260/343.3

*Primary Examiner*—Nicholas S. Rizzo
*Attorney, Agent, or Firm*—Fisher, Christen & Sabol

[57] ABSTRACT

A process is described for preparing triarylmethane derivatives of a high purity in an extremely high yield from 3-phenylphthalide derivatives and aniline derivatives or indole derivatives with Friedel-Crafts type catalyst or Friedel-Crafts type catalyst and an oxidizing agent.

8 Claims, No Drawings

TRIARYLMETHANE DERIVATIVES

This is a continuation of application Ser. No. 774,613, filed Mar. 4, 1977, which is a division of Ser. No. 699,584, filed June 24, 1976, now U.S. Pat. No. 4,045,458.

BACKGROUND OF THE INVENTION

This invention relates to a process for preparing colourless chromogenic compounds which form coloured markings upon contact with acidic materials by electron donor-acceptor colour-forming reaction.

Particularly, this invention relates to a novel process for preparing triarylmethane derivatives represented by the following general formulae (I), (II), (III) and (IV):

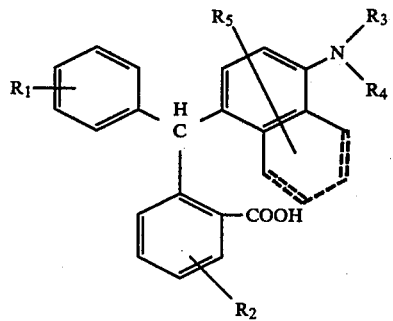
(I)

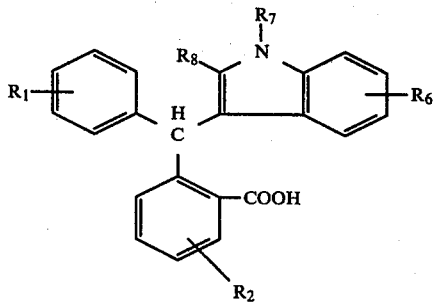
(II)

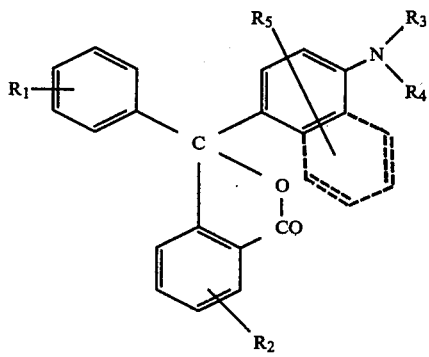
(III)

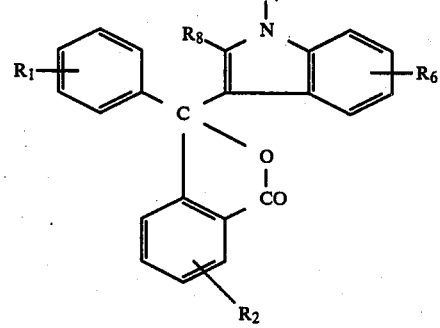
(IV)

wherein each of $R_1$ and $R_2$ is at least one hydrogen, halogen, nitro group, alkyl group, substituted alkyl group, amino group, substituted amino group, hydroxyl group, substituted hydroxyl group, thiohydroxyl group, or substituted thiohydroxyl group; each of $R_3$ and $R_4$ is hydrogen, substituted or unsubstituted alkyl group, cycloalkyl group, substituted or unsubstituted aralkyl group, substituted or unsubstituted aryl group, or substituted or unsubstituted unsaturated alkyl group, or one or both of $R_3$ and $R_4$ together with the adjacent nitrogen atom may form a heterocyclic ring: $R_5$ is at least one of hydrogen, halogen, alkyl group, nitro group, substituted or unsubstituted amino group, substituted or unsubstituted hydroxyl group, substituted or unsubstituted thiohydroxyl group; $R_6$ is at least one of hydrogen, halogen, lower alkyl group, lower alkoxyl group, amino group, lower alkylamino group, nitro group, phenyl group or phenoxy group; $R_7$ is hydrogen, alkyl group, aralkyl group or phenyl group; and $R_8$ is lower alkyl group or substituted or unsubstituted phenyl group.

There are known several methods for preparing triarylmethane derivatives represented by the general formula (I), for example, U.S. Pat. No. Re 23,024 discloses a method in which the triarylmethane derivative is prepared from m-dimethylamino-benzoic acid and Michler's hydrol by condensation reaction. Another method for preparing triarylmethane derivative by condensation reaction of dimethylaniline with o-phthalaldehydric acid is described in "Beilsteins Handbuch der Organische Chemie". Vol. 14, page 549. However, these methods give triarylmethane derivative in low yields because a large amount of by-products is produced. Furthermore, these methods give only limited compound having a symmetrical structure.

The triarylmethane derivatives having the general formula (II) are novel compounds which are synthesized for the first time by this invention.

The known method for preparing triarylmethane derivatives represented by the general formula (III) and (IV) is disclosed in U.S. Pat. Nos. 2,443,092 and 2,597,965, "Beilsteins Handbuch der Organische Chemie", vol. 18, page: 617 and Moriga and Oda, "Kogyo Kagaku Zasshi", vol. 64, page 1226, (1961), in which triarylmethane derivatives are prepared from dimethylaniline and phthalic anhydride by condensation. Another method is described in U.S. Pat. Nos. 3,491,112 and 3,491,116 and in "Beilsteins Handbuch der Organische Chemie", vol. 18, pages 618–619, in which benzophenone-2-carboxylic acid is first prepared from dimethylaniline and phthalic anhydride and then triarylmethane derivative is prepared from the resultant benzophenone-2-carboxylic acid and either dimethylaniline derivative or indole derivative.

However, these methods also give triarylmethane derivatives in low yields because of the production of a large amount of by-products. Particularly when substituted phthalic anhydride is used, a large amount of isomers is produced as well, therefore, the yield is more lowered. In addition, substituted phthalic anhydride has such a disadvantage that it is not suitable for industrial production because the process for the production thereof is complicated.

An object of the invention is to provide a novel process for preparing triarylmethane derivatives of a high purity in an extremely high yield.

Other objects and advantages of the invention will become apparent from the following description.

SUMMARY OF THE INVENTION

According to the invention, triarylmethane derivatives represented by the following general formula (I) or (II) are prepared by making 3-phenylphthalide derivatives represented by the general formula (V) react with anilic derivatives represented by the general formula (VI) or with indole derivatives represented by the general formula (VII) in the presence of Friedel-Crafts Type Catalysts:

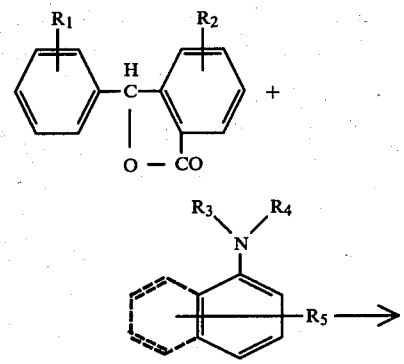
(V)

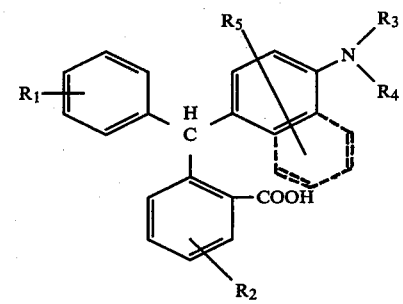
(VI)

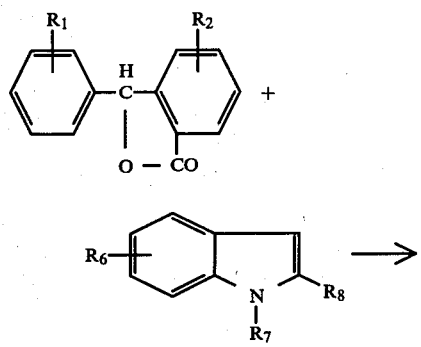
(I)

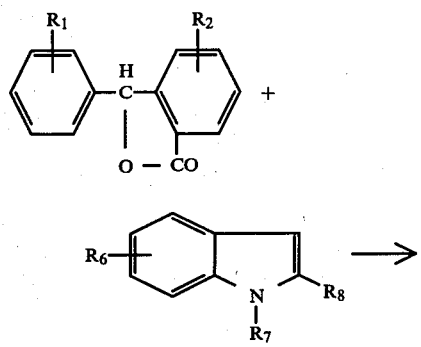

(V)

(VII)

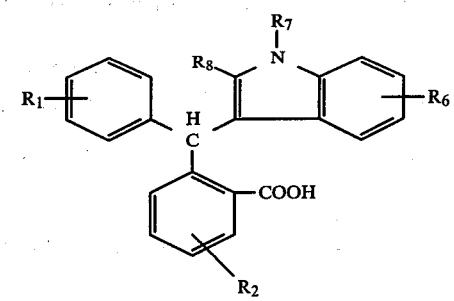
(II)

wherein $R_1$, $R_2$, $R_3$, $R_4$, $R_5$, $R_6$, $R_7$ and $R_8$ are the same as described above. Further, triarylmethane derivatives represented by the general formula (III) or (IV) are prepared by oxidizing the above obtained triarylmethane derivatives represented by the general formula (I) or (II) with use of oxidizing agents:

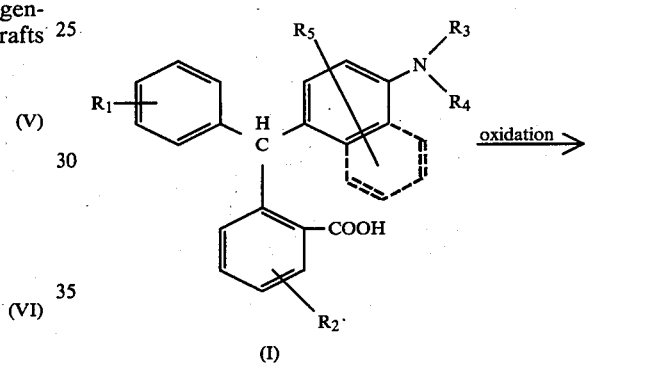
(I)

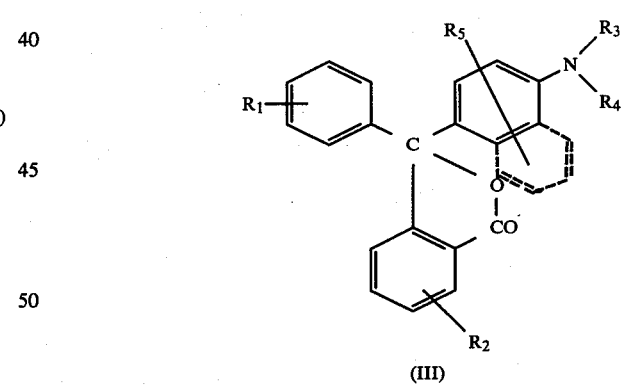
(III)

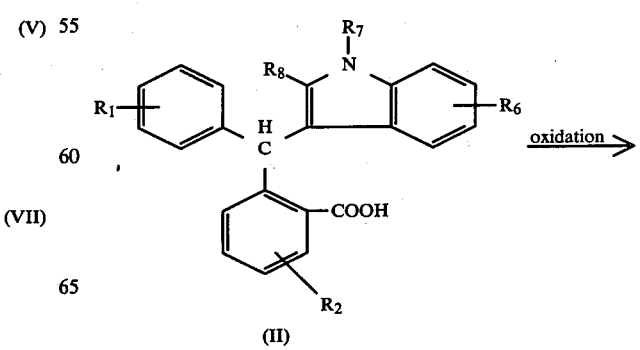
(II)

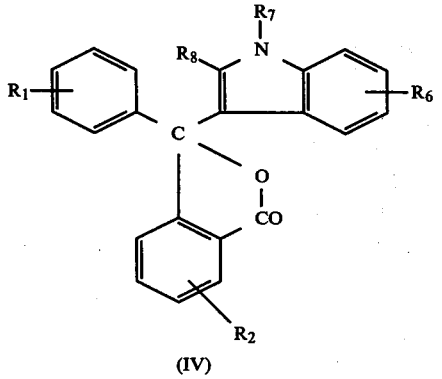

(IV)

wherein $R_1$, $R_2$, $R_3$, $R_4$, $R_5$, $R_6$, $R_7$ and $R_8$ are the same as described above.

DETAILED DESCRIPTION OF THE INVENTION 3-phenylphthalide derivative represented by the above described general formula (V) which is used in this invention is prepared, as shown as follows, from benzene derivative (VIII) and o-phthalaldehydic acid derivative (IX) by dehydration condensation, or from benzaldehyde derivative (X) and benzoic acid derivative (XI) by dehydration condensation:

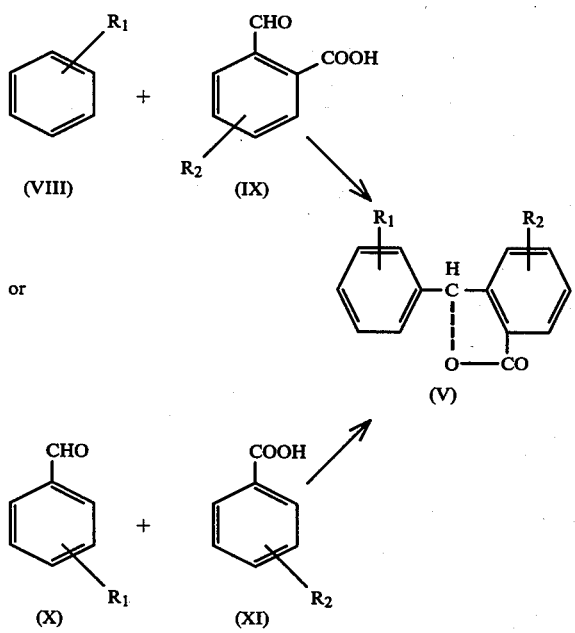

wherein $R_1$ and $R_2$ are the same as described above.

As the typical compounds of 3-phenylphthalide derivatives represented by the above general formula (V) which are used in this invention, the following compounds may be exemplified;
3-(4'-dimethylaminophenyl)phthalide,
3-(4'-dimethylamino-2'-methylphenyl)phthalide,
3-(4'-dimethylamino-2'-methoxyphenyl)phthalide,
3-(4'-dimethylamino-2'-methylthiophenyl)phthalide,
3-(4'-dimethylamino-2'-chlorophenyl)phthalide,
3-(4'-dimethylamino-2'-diethylaminophenyl)phthalide,
3-(4'-diethylaminophenyl)phthalide,
3-(4'-diethylamino-2'-chlorophenyl)phthalide,
3-(4'-diethylamino-2'-methoxyphenyl)phthalide,
3-[4'-(N-ethyl-N-benzyl)aminophenyl]phthalide,
3-[4'-(N-methyl-N-P-tolyl)aminophenyl]phthalide,
3-(4'-pyrrolidinophenyl)phthalide,
4-(julolidine-6'-yl)phthalide,
3-phenyl-6-dimethylaminophthalide,
3-phenyl-6-dimethylaminophthalide,
3-[2'(or 3', or 4')-methylphenyl]-6-dimethylaminophthalide,
3-[2'(or 3', or 4')-methoxyphenyl]-6-dimethylaminophthalide,
3-[2'(or 3', or 4')-methoxyphenyl]-6-diethylaminophthalide,
3-[2'-(or 3', or 4')-chlorophenyl]-6-dimethylaminophthalide,
3-[2'-(or 3', or 4')-nitrophenyl]-6-dimethylaminophthalide,
3-[2'-(or 3', or 4')-nitrophenyl]-6-diethylaminophthalide,
3-[2',3'(or 2',4')-dimethylphenyl]-6-dimethylaminophthalide,
3-[2',3'(or 2',4')-dimethoxyphenyl]-6-dimethylaminophthalide,
3-[2',3'(or 2',4')-dimethoxyphenyl]-6-diethylaminophthalide,
3-[2',3'(or 2',4')-dichlorophenyl]-6-dimethylaminophthalide,
3-(2'-methyl-4'-methoxyphenyl)-6-dimethylaminophthalide,
3-(2'-methoxy-4'-methylphenyl)-6-dimethylaminophthalide,
3-[2'(or 3', or 4')-dimethylaminophenyl]-6-dimethylaminophthalide,
3-[2'(or 3', or 4')-dimethylaminophenyl]-6-diethylaminophthalide,
3-[2'(or 3', or 4')-dimethylaminophenyl]-6-N-methyl-N-P-tolylaminophthalide,
3-[2'(or 3', or 4')-dimethylaminophenyl]-6-N-ethyl-N-benzylaminophthalide,
3-[(2'(or 3', or 4')-diethylaminophenyl]-6-dimethylaminophthalide,
3-[2'(or 3', or 4')-diethylaminophenyl]-6-diethylaminophthalide,
3-[2'(or 3', or 4')-dimethylaminophenyl]-5-chloro-6-dimethylaminophthalide,
3-[2'(or 3', or 4')-dimethylaminophenyl]-5-chloro-6-diethylaminophthalide,
3-[2'(or 3', or 4')-dimethylaminophenyl]-6-diallylaminophthalide,
3-[2'(or 3', or 4')-dimethylaminophenyl]-6-dipropargylamino-phthalide,
3-[2'(or 3', or 4')-dimethylaminophenyl]-6-pyrrolidinophthalide,
3-[2'(or 3', or 4')-dimethylaminophenyl]-6-pyrimidinophthalide,
3-[2'(or 3', or 4')-dimethylaminophenyl]-6-morpholinophthalide,
3-(4'-pyrrolidinophenyl)-6-dimethylaminophthalide,
3-(4'-pyrimidinophenyl)-6-dimethylaminophthalide,
3-(julolidine-6'-yl)-6-dimethylaminophthalide,
3-(4'-morpholinophenyl)-6-dimethylaminophthalide,
3-[4'-(N-methyl-N-benzyl)aminophenyl]-6-dimethylaminophthalide,
3-[4'-(N-methyl-N-benzyl)aminophenyl]-6-diethylaminophthalide,
3-[4'-(N-ethyl-N-benzyl)aminophenyl]-6-dimethylaminophthalide, 3-[4'-(N-methyl-N-para-tolyl)aminophenyl]-6-dimethylamino-phthalide,
3-[4'-(N-ethyl-N-para-tolyl)aminophenyl]-6-dimethylaminophthalide,
3-[4'-(N-ethyl-N-para-tolyl)aminophenyl]-6-diethylaminophthalide,
3-(4'-diallylaminophenyl)-6-dimethylaminophthalide,
3-(4'-dipropargylaminophenyl)-6-dimethylaminophthalide,
3-(4'-dimethylamino-2'-methylphenyl)-6-dimethylaminophthalide,
3-(4'-diethylamino-2'-methylphenyl)-6-dimethylaminophthalide,
3-(4'-dimethylamino-2'-chlorophenyl)-6-dimethylaminophthalide,
3-(4'-diethylamino-2'-chlorophenyl)-6-dimethylaminophthalide,
3-(4'-dimethylamino-2'-methoxyphenyl)-6-dimethylaminophthalide,
3-(4'-diethylamino-2'-methoxyphenyl)-6-dimethylaminophthalide,
3-(4'-dimethylamino-2'-methylthiophenyl)-6-dimethylaminophthalide,
3-(4'-diethylamino-2'-methylphenyl)-5-chloro-6-dimethylaminophthalide,
3-(4'-dietylamino-2'-methylphenyl)-5-chloro-6-diethylaminophthalide,
3-(4'-diethylamino-2'-methoxyphenyl)-5-chloro-6-dimethylaminophthalide,
3-(4'-diethylamino-2'-methoxyphenyl)-5-chloro-6-diethylaminophthalide,
3-(4'-dimethylaminophenyl)-6-methoxyphthalide,
3-(4'-diethylaminophenyl)-6-ethoxyphthalide,
3-(4'-diethylaminophenyl)-6-methoxyphthalide and
3-(4'-diethylamino-2'-methoxyphenyl)-6-methoxyphthalide.

Among the above mentioned 3-phenylphthalide derivatives, those having $R_2$ at the 6 position are preferably used and preferably $R_2$ is an substituted amino group.

Among the typical compounds of aniline derivatives represented by the above described general formula (VI) which are used in this invention there may be included the following compounds:

| aniline, | N—methylaniline, |
|---|---|
| N—ethylaniline, | o-toluidine, |
| m-toluidine, | m-nitroaniline, |
| m-phenylenediamine, | m-chloroaniline, |
| m-bromoaniline, | o-anisidine, |
| o-phenetidine, | 2.5-dichloroaniline, |
| N,N—dimethylaniline, | N,N—diethylaniline, |
| N—(2-ethylhexyl)-N—methylaniline, | |
| N,N—dibutylaniline, | N—dodecyl-N—ethylaniline, |
| N,N—diethyl-m-toluidine, | N,N—diethyl-o-toluidine, |
| N,N—dibenzylaniline, | N—methyl-N—benzylaniline, |
| N—ethyl-N—benzylaniline, | diphenylamine, |
| N—benzyldiphenylamine, | 4-benzyloxydiphenylamine, |
| N—ethyl-4-ethoxydiphenylamine, | |
| N—methyldiphenylamine, | N—ethyldiphenylamine, |
| N,N—diethyl-o-anisidine, | N,N—dimethyl-o-phenetidine, |
| N,N—diethyl-m-acetoxyaniline, | |
| N,N—dimethyl-m-nitroaniline, | |
| N,N—diethyl-m-nitroaniline, | |
| N,N—dimethyl-o-chloroaniline, | |
| N,N—dimethyl-m-chloroaniline, | |
| N,N—diethyl-m-chloroaniline, | |
| N,N—dimethyl-o-bromoaniline, | |
| N,N—dimethyl-m-bromoaniline, | |
| N,N—diethyl-o-bromoaniline, | |
| N,N—diethyl-m-bromoaniline, | |
| N,N—diethyl-m-hydroxyaniline, | |

-continued

| | |
|---|---|
| N,N—bis(β-cyanoethyl)aniline, | |
| N,N—bis(β-chloroethyl)aniline, | |
| N,N—bis(β-bromoethyl)aniline, | |
| N,N—bis(β-ethoxyethyl)aniline, | |
| N,N—bis(βL-cyanoethyl)-m-toluidine, | |
| N,N—bis(β-chloroethyl)-m-toluidine, | |
| N,N—bis(β-bromoethyl)-m-toluisine, | |
| N—ethyl-N—(β-chloroethyl)-m-toluidine, | |
| N,N—bis(β-ethoxyethyl)-m-toluisine, | |
| N—ethyl-N—phenethylaniline, | |
| N—ethoxycarbonylmethyl-N—cyclohexylaniline, | |
| N,N—diethyl-m-phenylenediamine, | |
| N,N—diethyl-o-phenylenediamine, | |
| N,N,N',N',—tetraethyl-m-phenylenediamine, | |
| N,N,N',N',—tetraethyl-o-phenylenediamine, | |
| N—cyclohexyl-N—methylaniline, | |
| N—phenylmorpholine, | N—phenylpiperidine, |
| N—phenylpyrrolidine, | N—phenylimidazoline, |
| N—phenylpyrazolidine, | N—phenylpiperazine, |
| julolidine, | 1-naphthylamine, |
| N—methyl-1-naphthylamine, | N—ethyl-1-naphthylamine, |
| N—phenyl-1-naphthylamine, | |
| N,N—dimethyl-1-naphthylamine, | |
| N,N—diethyl-1-naphthylamine, | |
| 5-chloro-N,N—dimethyl-1-naphthylamine, | |
| 5-bromo-N,N—dimethyl-1-naphthylamine, | |
| 5-ethoxy-N,N—diethyl-1-naphthylamine, | |
| 5-benzyloxy-N,N—dimethyl-1-naphthylamine, | |
| N—ethyl-N—benzyl-1-naphthylamine, | |
| N,N—bis(β-chloroethyl)-1-naphthylamine, | |
| N,N—bis(β-bromoethyl)-1-naphthylamine, | |
| N,N—bis(β-cyanoethyl)-1-naphthylamine, | |
| N,N—bis(β-methoxyethyl)-1-naphthylamine, | |
| N,N—bis(β-ethoxyethyl)-1-naphthylamine and | |
| N—phenyl-N—methyl-1-naphthylamine. | |

Among the typical compounds of indole derivatives represented by the above mentioned general formula (VII) which are used in this invention there may be included the following compounds:

| 2-methylindole, | 2-ethylindole, |
|---|---|
| 2-phenylindole, | 2-(2'-methylphenyl)indole, |
| 2-methyl-5-chloroindole, | 2-methyl-5-ethoxyindole, |
| 2-methyl-7-phenylindole, | 2-methyl-5-aminoindole, |
| 1,2-dimethylindole, | 1-methyl-2-phenylindole, |
| 1.2.5-trimethylindole, | 1.2-dimethyl-5-methoxyindole, |
| 1.2-dimethyl-5-phenoxyindole, | |
| 1.2-dimethyl-5-nitroindole, | |
| 1-methyl-2-(4'-chlorophenyl)indole, | |
| 1-methyl-2-(4'-ethoxyphenyl)indole, | |
| 1-methyl-2-(4'-ethoxyphenyl)-5-dimethylaminoindole, | |
| 1-benzyl-2-methylindole, | 1-benzyl-2.5-dimethylindole |
| 1-benzyl-2-methyl-5-methoxyindole, | |
| 1.2-dimethyl-7-phenylindole, | |
| 1-phenyl-2.5-dimethylindole, | |
| 1-phenyl-2.5-diethylindole and | |
| 1.2-dimethyl-5.6-dichloroindole. | |

In the practice of the invention, 3-phenylphthalide derivative is made to react with aniline derivative or indole derivative in the presence of Friedel-Crafts type catalyst, if necessary, with use of a suitable solvent, at the temperature of 0° to 180° C. for the period between several minutes and several decades of hours.

As a Friedel-Crafts type catalyst, acidic halide Lewis acid catalysts such as $AlCl_3$, $AlBr_3$, $BeCl_2$, $CdCl_2$, $ZnCl_2$, $BF_3$, $BCl_3$, $GaCl_3$, $GaBr_3$, $TiCl_4$, $TiBr_4$, $ZnCl_4$, $SnCl_4$, $SnBr_4$, $SbCl_5$, $SbCl_3$, $BiCl_3$, $FeCl_3$, $UCl_4$, $PF_5$, $SbF_5$, $AsF_5$ and mixed pentafluorides of Nb and Ta; metal alkyl Lewis acid catalysts such as $Al_2Cl_3(CH_3)_3 + HCl$, $AlCl_2(C_2H_5)$, $AlCl(C_2H_5)_2$, $AlBr_3(C_2H_5)_3$, $Al(C_2H_5)_2Br$, $Al(C_2H_5)Br_2$, $Al(C_2H_5)_3$, $Al(t-C_4H_9)_3$, $Al(i-C_4H_9)_3$, $AuBr_2C_2H_5$, $Be(C_2H_5)_2$, $BRx_3$, $MgRx_2$, $Rx_2Mg \cdot MgX_2$, $TiCl_3CH_3$, $TiCl_3(C_2H_5)$ and $Zn(C_2H_5)_2$, wherein Rx is alkyl group and X is halogen; metal alkoxide Lewis acid catalysts such as $Al(OC_6H_5)_3$, aluminum alkoxides, $AlCl_2ORx$, $AlCl_3$·$Ti(ORx)_4$, $Ti(BuO)_4$ and $Ti(i—PrO)_4$, wherein Rx is alkyl group; Brønsted acid catalysts such as, phosphoric acid, polyphosphoric acid, perchloric acid, chlorosulfonic acid, fluorosulfonic acid, alkane sulfonic acids such as ethane sulfonic acid, p-toluenesulfonic acid, acetic acid, chloroacetic acids, trifluoroacetic acid, sulfuric acid, hydrogen halides and alkyl halides; acidic oxide and sulfide (acidic chalcide) catalysts such as alumina, $Al_2O_3$·CaO, $Al_2O_3$·$Cr_2O_3$, $Al_2O_3$·$Fe_2O_3$, $Al_2O_3$·$V_2O_3$, alumino-silicates (natural), bauxite, bentonite clay, BeO, acid activated clay, chromia (with silica-alumina), $Cr_2O_3$(synthetic), $Cr_2O_3$, $Fe_2O_3$, floridin, Georgia clay, Gumbrin clay, magnesia (with silica-alumina), molybdenum oxide-alumina, $MoS_2$, $MoS_3$, $MoS_2$·CoS, montmorillonite clay, nickel-alumina, $P_2O_5$, silica-alumina, thoria (with silica-alumina), $ThO_2$(synthetic), $TiO_2$, $WO_3$ (with silica-alumina) and zirconia (with silica-alumina); acidic cation exchanger catalysts such as sulfonated coals, sulfonated phenol-formaldehyde resins, sulfonated divinylbenzene cross linked polymers and exchangers with carboxyl group, phenol group or alumina-silicate skeleton; metathetic cation forming substances such as $AgAsF_6$, $AgClO_4$, $AgBF_4$, $AgNO_3$, $AgOOCCF_3$, $AgPO_4$, $AgPF_6$, $AgSbF_6$, $Ag_2SO_4$, $AgNbF_6$, $AgTaF_6$ and $AgTi_2F_9$; and the mixtures thereof may be used.

Among the above Friedel-Crafts type catalyst acidic halide Lewis acid catalysts, Brønsted acid catalysts, acidic oxide catalysts, metal alkyl Lewis acid catalysts and metal alkoxide acid catalysts are previously used because they are highly reactive and economical. Particularly, acidic halide Lewis acid catalysts, Brønsted acid catalysts and acidic oxide catalysts are most preferable.

Referring to the amount of such Friedel-Crafts type catalysts, it may be controlled properly according to the kinds of the starting materials, but it is preferable to use them in amounts equimolar with respect to 3-phenylphthalide derivative or more.

As a solvent, benzene, toluene, alkylbenzene, chlorobenzene, dichlorobenzene, bromobenzene, nitrobenzene, alkylnaphthalene, ethylene chloride, chloroform, tetrachloromethane, tetrachloroethane, nitromethane, nitroethane, nitropropane, carbon disulfide, kerosene, high-boiling naphtha, etc. are preferably used. In order to increase the rate of reaction and to minimize the amount of catalyst, it is preferable that such a solvent should not be used or the amount of the solvent should be minimized even when it is used. On the other hand, the excess amount of solvent is preferably used for the purpose of control of the reaction temperature, homogenization of reaction, extraction or the resultant product, etc. Therefore, the solvent should be used as occasion demands.

In this invention, triarylmethane derivatives represented by the general formula (III) or (IV) are obtained by oxidation of the above obtained triarylmethane derivatives represented by the general formula (I) or (II) with use of an oxidizing agent. Triarylmethane derivative represented by the general formula (I) or (II) is dissolved in acidic aqueous solutions such as hydrochloric acid solution and sulfuric acid solution, alkaline aqueous solutions such as caustic soda solution and caustic potash solution, or organic solvents such as alcohols, lower aliphatic carboxylic acids, ethers, ketones, aromatic hydrocarbons, and thereafter an oxidizing agent is added to the solution, and then the oxidation is carried out at the temperature of 0° to 500° C. for the period between several minutes and several decades of hours.

As an oxidizing agent, manganese compounds such as permanganates, manganates, managanese dioxide, manganese (III) salts and manganese acetate; chromic acid corn pounds such as chromic anhydride, chromic acid, perchromates, alkyl esters of chromic acid and chromyl chloride; lead compounds such as PbO, $PbO_2$ and $Pb(OCOCH_3)_4$; copper compounds such as CuO, $Cu(OH)_2$, $CuSO_4$, $Cu(OCOCH_3)_2$, $CuCl_2$ and $CuBr_2$; cobalt compounds such as $Co_2(SO_4)_3$ and $Co_3O_4$; cerium compounds such as $CeO_2$, $Ce(SO_4)_2$ and $Ce(SO_4)_3$; bismuth compounds such as $NaBiO_3$, BiO and $Bi(OCOCH_3)_2$; silver compounds such as $Ag_2O$, $AgOCOCH_3$ and $AgNO_3$; iron compounds such as $FeCl_3$, $Fe_2(SO_4)_3$ and potassium ferricyanate; $SeO_2$; $RuO_4$; $OsO_4$; inorganic peroxides such as hydrogen peroxide, Fenton's reagent, persulfuric acid and salts thereof; organic peroxides such as performic acid, peracetic acid, perpropionic acid, perbutyric acid, perbenzoic acid, monoperphthalic acid, monoperterephthalic acid, monopersuccinic acid and trifluoroperacetic acid; halides such as hypochlorites, chlorates, hypobromites and bromates; oxygen; ozone; ultraviolet ray; sulfoxides; amine oxides; and chloranil are preferably used. The amount of oxidizing agent may be controlled according to the kinds of oxidizing agent to be used, but it may be usually used in an excess of a stoichiometric amount based on the amount of said triarylmethane derivatives having the general formula (I) or (II).

When the compounds having an oxidizing function such as $FeCl_3$, $FeBr_3$, $AgNO_3$, $CuCl_2$ and peracetic acid are used as a Friedel-Crafts type catalyst in the preparation of triarylmethane derivatives represented by the general formula (I) or (II) from 3-phenylphthalide derivatives and aniline derivatives or indole derivatives, the resultant triarylmethane derivatives represented by the general formula (I) or (II) are instantaneously oxidized to form triarylmethane derivatives represented by the general formula (III) or (IV).

Namely, the reaction of a 3-phenylphthalide derivative with an aniline derivative or an indole derivative to form a triarylmethane derivative having the general formula (I) or (II) is immediately followed by and concurrently occurs with the oxidizing reaction to form said triarylmethane derivative having the general formula (III) or (IV). For this purpose Friedel-Crafts type catalysts may preferably be used in an excess of the total amount of an equimolar amount with respect to said 3-phenylphthalide derivative and a stoichiometric amount based on the amount of said triarylmethane derivative having the general formula (I) or (II)

The process of the invention for the preparation of triarylmethane derivatives from 3-phenylphthalide derivatives is a novel method which has never been described in any literature. The process of the invention gives triarylmethane derivatives at high purities and in extremely high yields. In addition, the process of the invention makes it possible to prepare the various novel triarylmethane derivatives which could not be synthesized by any conventional methods.

The triarylmethane derivatives obtained in this invention form coloured markings upon contact with acidic substances such as solid acids, e.g., acid clay, activated clay, attapulgite, zeolite, kaolin, bentonite and silicates;

and organic acidic materials such as phenol-formaldehyde polymers, phenol-acetylene polymers, maleic acid rosin resin, ethylene-maleic acid anhydride polymers, salicylic acid-aldehyde polymers, salicylic acid-acetylene polymers, polyvalent metal salts of those polymers mentioned above, aromatic carboxylic acids, e.g., salicylic acid and salicylic acid derivatives, and polyvalent metal salts of aromatic carboxylic acids by an electron donor-acceptor colour-forming reaction, therefore, they may be utilized as colourless chromogenic compounds (i.e. electron donor) in various fields which utilize such a reaction. For example, triarylmethane derivatives of the invention can be utilized for the production of pressure sensitive copying sheet which is disclosed in U.S. Pat. Nos. 2,730,456 and 2,730,457 and Japanese Pat. No. 511,757, heat sensitive copying sheet which is disclosed in U.S. Pat. Nos. 3,451,338 and 3,539,375, hectographic copying sheet, electron beam sensitive recording sheet, photosensitive sheet, electrographic heat sensitive recording sheet, ultrasonic recording sheet, toner for Xerox type copying sheet, and leuco ink.

PREFERRED EMBODIMENT OF THE INVENTION

The following examples serve to illustrate the invention in more detail although the invention is not limited to the examples.

EXAMPLE 1

30 g of 3-(p-dimethylaminophenyl)-6-dimethylaminophthalide and 13 g of dimethylaniline were dissolved in 250 cc of tetrachloroethane. 14 g of anhydrous aluminum chloride was added to the solution and the resultant mixture was heated at 50° C. for 3 hours with stirring. After the termination of reaction, 30% aqueous solution of caustic soda was added to dissolve aluminum chloride while cooling the mixture with ice. Then, the tetrachloroethane phase was separated with the aid of a separatory funnel, and then steam distilled to remove the unreacted dimethylaniline and tetrachloroethane. The remaining aqueous phase was neutralized with acetic acid to obtain a pale yellow solid. The yield was 42 g. This solid was recrystallized from benzene to obtain colourless crystals having a melting point (hereinafter referred to as m.p.) of 201° C. The obtained crystal results in a blue colouration when it is subjected to light on silica gel. This compound is triarylmethane represented by the following formula:

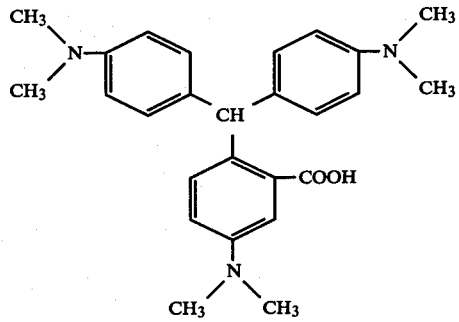

EXAMPLE 2

30 g of 3-(p-dimethylaminophenyl)-6-dimethylaminophthalide and 17 g of N,N-diethyl-m-toluidine were dissolved in 300 cc of benzene. After the addition of 14 g of zinc chloride, the mixture was heated at 80° C. for 5 hours with stirring. After cooling, the resultant precipitate was filtered and then dried. The obtained precipitate was dissolved in dilute hydrochloric acid, and then the pH of the solution was adjusted at 4.0 with an aqueous solution of caustic soda to form a yellow precipitate. This precipitate was filtered and then dried. The yield was 45 g. Recrystallization from benzene gave triarylmethane represented by the following formula in the form of colourless crystals whose m.p. was 255°-260° C. This compound turns in blue colour upon exposure to light on TCL.

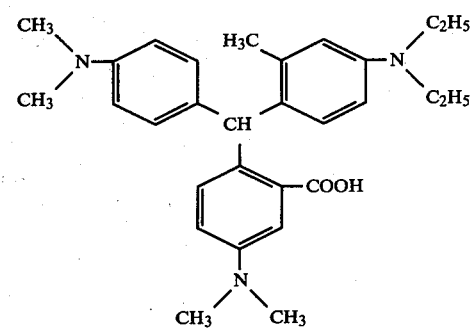

EXAMPLE 3

Example 1 was repeated except that 26 g of 3-(p-dimethylaminophenyl)phthalide was used instead of 30 g of 3-(p-dimethylaminophenyl)-6-dimethylaminophthalide to obtain 32 g of triarylmethane represented by the following formula whose m.p. was 194°-195° C. in the form of colourless crystals. This compound becomes bluish green upon exposure to light on silica gel.

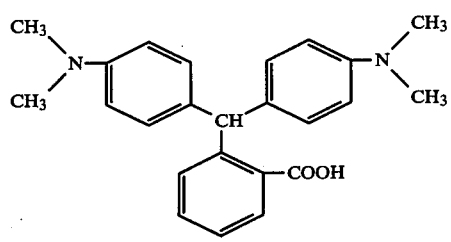

EXAMPLE 4

Example 1 was repeated except that 29 g of 3-(o-methoxyphenyl)-6-dimethylaminophthalide was used instead of 30 g of 3-(p-dimethylaminophenyl)-6-dimethylaminophthalide to obtain 38 g of triarylmethane represented by the following formula whose m.p. was 237°-238° C. in the form of colourless crystals (Recrystallized from acetic acid-methanol). This compound becomes bluish green upon exposure to light on silica gel.

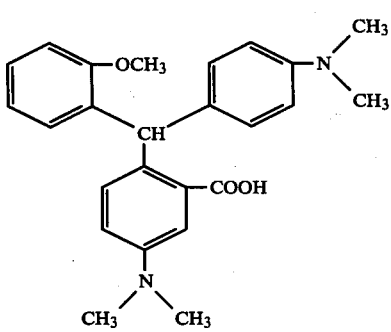

EXAMPLE 5

Example 1 was repeated except that 13.5 g of 2-methylindole was used instead of 13 g of dimethylaniline to obtain 34 g of triarylmethane having the following formula in the form of colourless crystals. This compound becomes violet upon exposure to light silica gel.

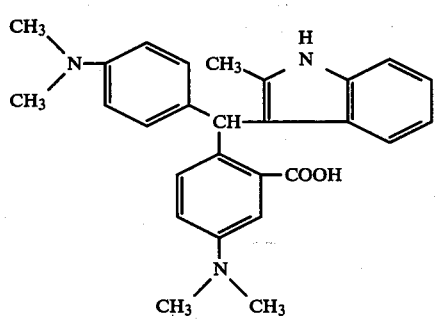

EXAMPLE 6

Example 1 was repeated except that 29 g of 3-(o-methoxyphenyl)-6-dimethylaminophthalide and 13.5 g of 2-methylindole were used instead of 30 g of 3-(p-dimethylaminophenyl)-6-dimethylaminophthalide and 13 g of dimethylaniline, respectively, to obtain 29 g of triarylmethane having the following structure whose m.p. was 203°–205° C. in the form of colourless crystals (Recrystallized from methanol). This compound becomes blue black upon exposure to light on silica gel.

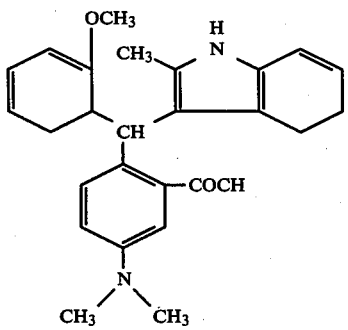

EXAMPLE 7

Example 1 was repeated except that 32 g of 3-(3′,4′-dimethoxyphenyl)-6-dimethylaminophthalide and 13.5 g of 2-methylindole were used, respectively, instead of 30 g of 3-(p-dimethylaminophenyl)-6-dimethylaminophthalide and 13 g of dimethylaniline to obtain 33 g of triarylmethane having the following structure whose m.p. was 230°–232° C. in the form of colourless crystals (Recrystallized from methanol). This compound becomes bluish violet upon exposure to light on silica gel.

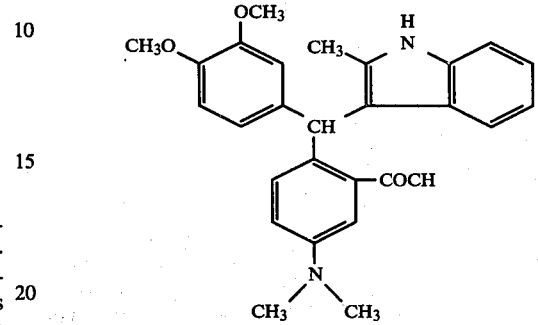

EXAMPLE 8

Example 1 was repeated except that 19.5 g of 2-phenylindole was used instead of 13 g of dimethylaniline to obtain 34 g of triarylmethane having the following structure in the form of colourless crystals. This compound becomes blue upon exposure to light on silica gel.

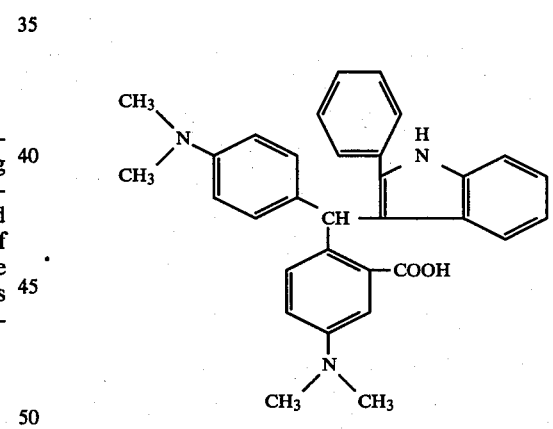

EXAMPLE 9

Example 1 was repeated except that 32 g of 3-(2′,4′-dimethoxyphenyl)-6-dimethylaminophthalide and 13.5 g of 2-methylindole were used, respectively, instead of 30 g of 3-(p-dimethylaminophenyl)-6-dimethylaminophthalide and 13 g of dimethylaniline to obtain 27 g of triarylmethane having the following structure whose m.p. was 202°–203° C. in the form of colourless crystals (Recrystallized from methanol). This compound becomes bluish violet upon exposure to light on silica gel.

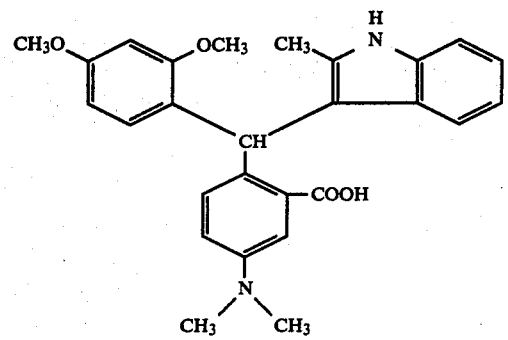

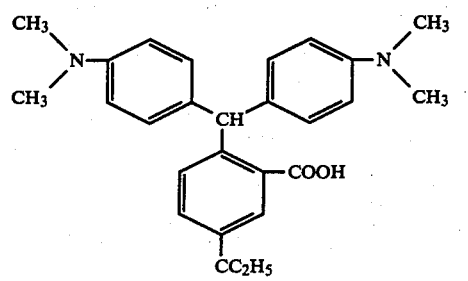

EXAMPLE 10

Example 1 was repeated except that 30 g of 3-(p-dimethylaminophenyl)-6-ethoxyphthalide was used instead of 30 g of 3-(p-dimethylaminophenyl)-6-dimethylaminophthalide to obtain 39 g of triarylmethane having the following structure whose m.p. was 197°–198° C. in the form of colourless crystals. This compound becomes bluish green upon exposure to light on silica gel.

EXAMPLE 11

Example 1 was repeated with use of the various starting materials and catalysts shown in the following table instead of 3-(p-dimethylaminophenyl)-6-dimethylaminophthalide, dimethylaniline and anhydrous aluminum chloride to obtain the various triarylmethane compounds shown in the following table. The colours formed upon exposure to light on silica gel are shown in the following table as well.

| 3-phenylphthalide derivatives | aniline or indole derivatives | catalysts | resultant compounds | color |
|---|---|---|---|---|
| [structure: bis(diethylamino) phenylphthalide] | N,N-diethylaniline ($C_2H_5$)$_2$NC$_6$H$_5$ | ZnCl$_2$ | [triarylmethane with two $N(C_2H_5)_2$ groups and $N(CH_3)_2$, COOH] | Blue |
| [structure: dimethylamino/dibutylamino phenylphthalide] | N,N-dimethylaniline | " | [triarylmethane with two $N(CH_3)_2$ and $N(C_4H_9)_2$, COOH] | " |
| [structure: with CH$_3$, N-methyl-N-benzyl phenylphthalide] | " | " | [triarylmethane with two $N(CH_3)_2$ and N(CH$_3$)(CH$_2$C$_6$H$_5$), COOH] | " |

-continued

| 3-phenylphthalide derivatives | aniline or indole derivatives | catalysts | resultant compounds | color |
|---|---|---|---|---|
| (structure) | " | " | (structure) | " |
| (structure) | " | " | (structure) | " |
| (structure) | " | Ti(i-PrO)$_4$ | (structure) | " |
| (structure) | " | SiO$_2$—Al$_2$O$_3$ | (structure) | Bluish green |
| (structure) | " | " | (structure) | Bluish green |
| (structure) | (structure) | ZnCl$_2$ | (structure) | Blue black |

-continued

| 3-phenylphthalide derivatives | aniline or indole derivatives | catalysts | resultant compounds | color |
|---|---|---|---|---|
| 4-dimethylamino-phenyl / 3-nitro phthalide derivative | N,N-dimethylaniline | " | triarylmethane with COOH and NO₂ | Bluish green |
| 4-dimethylamino / 4-dimethylamino phthalide | N-methyl-N-dodecylaniline | Al(C₂H₅)₃ | triarylmethane product with C₁₂H₂₅ | Blue |
| bis(4-dimethylamino) phthalide | 2,2-dimethyl-1,3-dimethyl-perimidine (naphthalene-fused) | ZnCl₂ | corresponding product | Blue black |
| bis(4-dimethylamino) phthalide | N,N-dimethylaniline | " | triarylmethane product | Bluish green |
| bis(4-dimethylamino) phthalide | N-methylaniline | CH₃COOH | product with NHCH₃ | Blue |
| bis(4-dimethylamino) phthalide | 3-chloro-N,N-dimethylaniline | CF₃COOH | product with Cl | " |

| 3-phenylphthalide derivatives | aniline or indole derivatives | catalysts | resultant compounds | color |
|---|---|---|---|---|
| [structure: bis(dimethylamino)phenyl phthalide] | $C_2H_5$-N($C_2H_5$)-C$_6$H$_4$-OCH$_3$ | $SiO_2$ | [triarylmethane with OCH$_3$, N(CH$_3$)$_2$, N($C_2H_5$)$_2$, COOH, N(CH$_3$)$_2$] | " |
| [chloro-bis(dimethylamino)phenyl phthalide] | $CH_3$-N($CH_3$)-C$_6$H$_4$-SCH$_3$ | Clay (acid activated) | [triarylmethane with Cl, SCH$_3$, N(CH$_3$)$_2$ groups, COOH, N(CH$_3$)$_2$] | Blue |

EXAMPLE 12

Example 1 was repeated except that 33 g of anhydrous ferric chloride was used instead of 14 g on anhydrous aluminum chloride to obtain 16 g of compound having the following structure whose m.p. was 180° C. in the form of colourless crystals (Recrystallized from benzene-methanol). This compound becomes blue upon contact with silica gel.

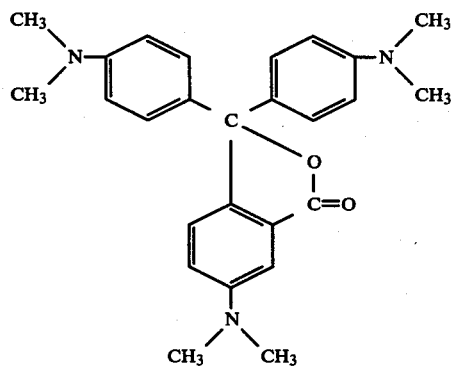

EXAMPLE 13

Example 12 was repeated with use of the various starting materials and catalysts shown in the following table instead of 3-(p-dimethylaminophenyl)-6-dimethylaminophthalide, dimethylaniline and anhydrous ferric chloride to obtain the various triarylmethane compounds shown in the following table. Those compounds produce the various colours shown in the following table immediately upon contact with silica gel.

| 3-phenylphthalide derivatives | aniline or indole derivatives | catalysts | resultant compounds | color |
|---|---|---|---|---|
| [bis(dimethylamino)phenyl phthalide structure] | $C_2H_5$-N($C_2H_5$)-C$_6$H$_5$ | $FeBr_3$ | [triarylmethane phthalide with N(CH$_3$)$_2$, N($C_2H_5$)$_2$, N(CH$_3$)$_2$] | Blue |

| 3-phenylphthalide derivatives | aniline or indole derivatives | catalysts | resultant compounds | color |
|---|---|---|---|---|
| (structure) | (structure) | CuCl₂ | (structure) | Blue |
| (structure) | (structure) | FeCl₃ | (structure) | Blue |
| (structure) | (structure) | AgNO₃ | (structure) | Violet |

EXAMPLE 14

33 g of 3-(m-diethylaminophenyl)-6-dimethylaminophthalide and 13 g of dimethylaniline were dissolved in 300 cc of tetrachloroethane. 14 g of anhydrous aluminum chloride was added to the solution, and then the mixture was heated at 50° C. for 3 hours with stirring. After the termination of reaction, 30% aqueous solution of caustic soda was added to the mixture to dissolve aluminum chloride while cooling with ice. Tetrachloroethane phase was steam distilled to remove unreacted dimethylaniline and tetrachloroethane. The remaining aqueous phase was neutralized with acetic acid to obtain a white solid. This solid was dissolved in 600 cc of 2.5% aqueous solution of caustic soda, and then heated at 50° C. 600 cc of 5% aqueous solution of potassium persulfate was added dropwise to the above solution, and then the mixture was heated at 60° C. for 3 hours. After the termination of reaction, the resultant precipitates were filtered and recrystallized from methanol to obtain 31 g of 3-(m-diethylaminophenyl)-3-(p-dimethylaminophenyl)-6-dimethylaminophthalide having the following structure whose m.p. was 177°–178° C. in the form of colourless crystals. This compound become green on contact with silica gel.

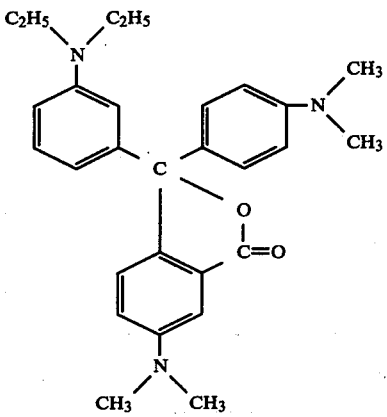

EXAMPLE 15

Example 14 was repeated except that 29 g of 3-(p-methoxyphenyl)-6-dimethylaminophthalide and 19.5 g of 2-phenylindole were used, respectively, instead of 33 g of 3-(m-diethylaminophenyl)-6-dimethylaminophthalide and 13 g of dimethylaniline to obtain 24 g of 3-(p-methoxyphenyl)-3-(2-phenylindole-3-yl)-6-dimethylaminophthalide having the following structure whose m.p. was 224°–225° C. in the form of colourless crystals (Recrystallization from benzene-methanol).

This compound becomes blue black on contact with silica gel.

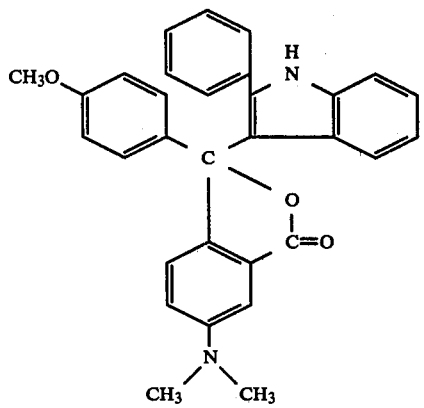

EXAMPLE 16

Example 14 was repeated except that 32 g of 3-(3,4-dimetoxyphenyl)-6-dimethylaminophthalide and 19.5 g of 2-phenylindole were used instead of 33 g of 3-(m-diethylaminophenyl)-6-dimethylaminophthalide and 13 g of dimethylaniline to obtain 21 g of 3-(3',4'-dimetoxyphenyl)-3(2'-phenylindole-3'-yl)-6-dimethylaminophthalide having the following structure whose m.p. was 235°–236° C. in the form of colourless crystals (Recrystallized from benzene-methanol). This compound becomes blue black upon contact with silica gel.

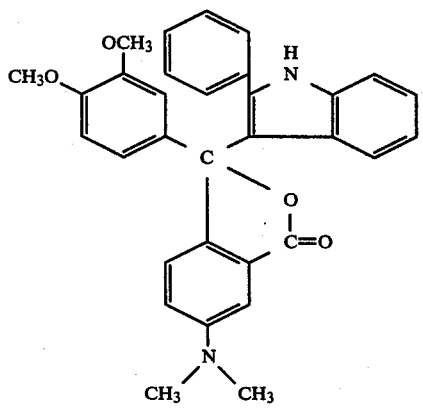

EXAMPLE 17

Example 14 was repeated except that 32 g of 3-(2',4'-dimethoxyphenyl)6-dimethylaminophthalide and 19.5 g of 2-phenylindole were used instead of 33 g of 3-(m-diethylaminophenyl)6-dimethylaminophthalide and 13 g of dimethylaniline to obtain 30 g of 3-(2',4'-dimethoxyphenyl)-3-(2'-phenylindole-3'-yl)-6-dimethylaminophthalide having the following structure whose m.p. was 239°–240° C. in the form of colourless crystals (Recrystallized from benzene-methanol). This compound becomes blue black upon contact with silica gel.

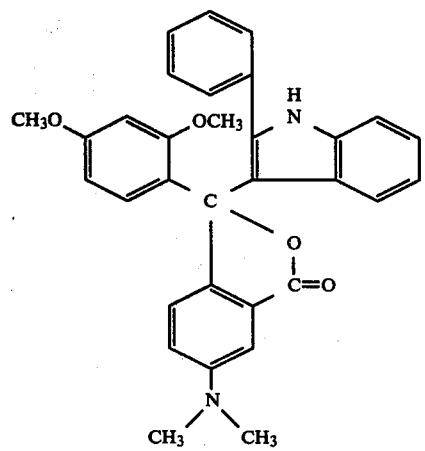

EXAMPLE 18

Example 14 was repeated except that 35 g of 3-(julolidine-6'-yl)phthalide and 15 g of 1,2-dimethylindole were used instead of 33 g of 3-(m-diethylaminophenyl)-6-dimethylaminophthalide and 13 g of dimethylaniline to obtain 28 g of 3-(julolidine-6'-yl)-3-(1',2'-dimethylindole-3'-yl)phthalide having the following structure whose m.p. was 259°–260° C. in the form of colourless crystals (Recrystallized from alcohol). The compound becomes violet upon contact with silica gel.

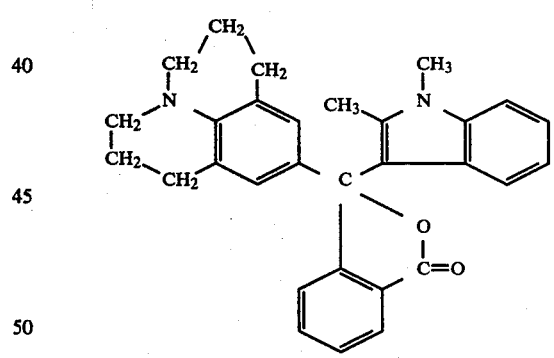

EXAMPLE 19

Example 14 was repeated except that 38 g of 3-{p-di(n-butyl)aminophenyl}phthalide and 15 g of 1,2-dimethylindole were used instead of 33 g of 3-(m-diethylaminophenyl)-6-dimethylaminophthalide and 13 g of dimethylaniline to obtain 33 g of 3-{p-di(n-butyl)aminophenyl}-3-(1',2'-dimethylindole-3'-yl)phthalide having the following structure whose m.p. was 140°–142° C. in the form of colourless crystals (Recrystallized from benzene-methanol). This compound becomes violet on contact with silica gel.

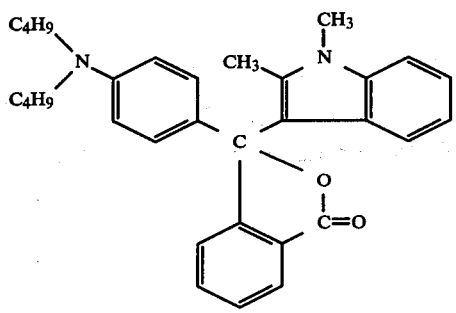

EXAMPLE 20

Example 14 was repeated with use of the following various 3-phenylphthalide derivatives instead of 3-(m-diethylaminophenyl)-6-dimethylaminophthalide, and the following various aniline or indole derivatives instead of dimethylaniline to obtain the triarylmethane derivatives shown in the following table. The colours which were formed on contact with silica gel are shown in the following table as well.

| 3-phenylphthalide derivatives | aniline indole derivatives | resultant compound | m.p. | color |
|---|---|---|---|---|
| [structure] | [structure] | [structure] | 89–93° C. | Blue |
| " | [structure] | [structure] | 147–149° C. | " |
| " | [structure] | [structure] | 187–189° C. | " |

-continued
| 3-phenylphthalide derivatives | aniline indole derivatives | resultant compound | m.p. | color |
|---|---|---|---|---|
| '' | 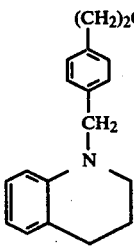 | 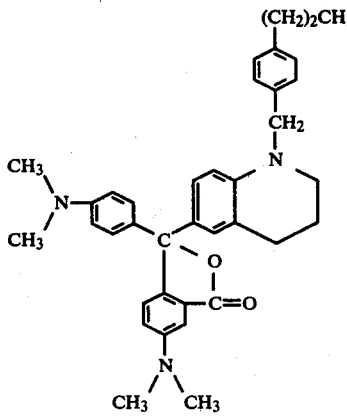 | 68–70° C. | '' |
| '' | 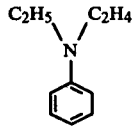 | 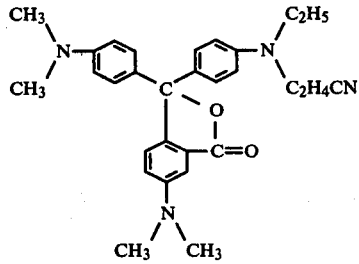 | — | '' |
| '' | 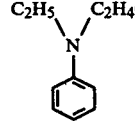 | 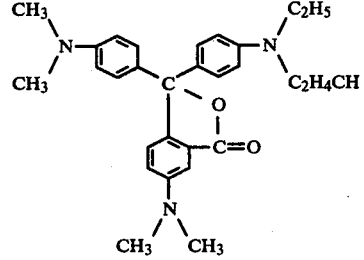 | — | '' |
| '' | 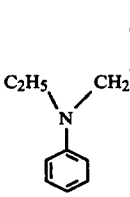 | 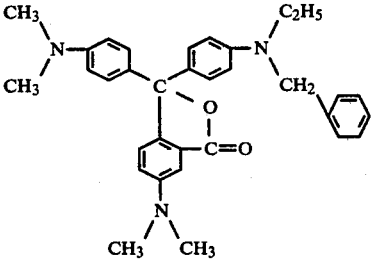 | 143–145° C. | '' |
| '' | 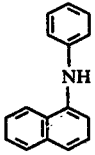 | 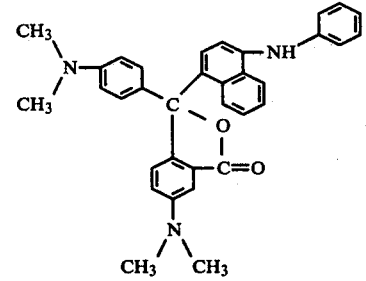 | — | Green |

-continued
| 3-phenylphthalide derivatives | aniline indole derivatives | resultant compound | m.p. | color |
|---|---|---|---|---|
| " | 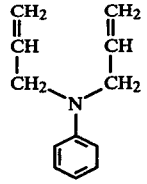 | 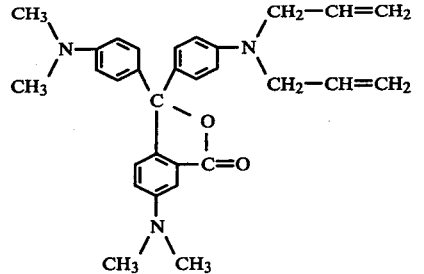 | — | Blue |
| " | 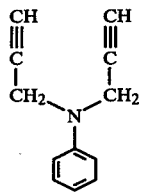 | 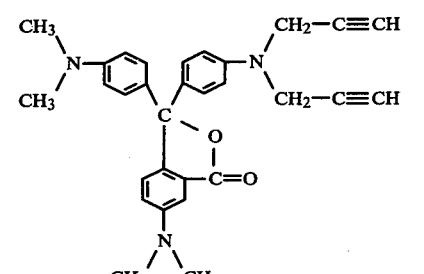 | — | " |
| " | 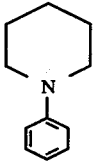 | 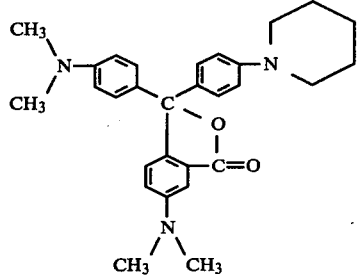 | — | " |
| " | 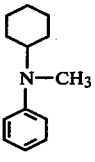 | 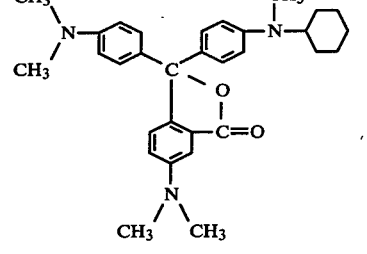 | — | " |
| 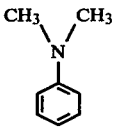 | 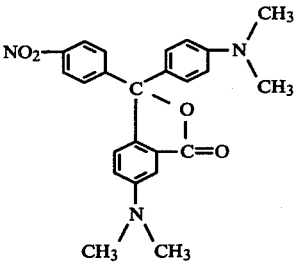 | | — | Bluish green |

-continued

| 3-phenylphthalide derivatives | aniline indole derivatives | resultant compound | m.p. | color |
|---|---|---|---|---|
| [structure: 2-chlorobenzyl with dimethylamino phthalide] | " | [structure] | — | Bluish green |
| [structure: benzyl with dimethylamino phthalide] | " | [structure] | — | Bluish green |
| [structure: 4-chlorobenzyl with diethylamino phthalide] | N,N-diethyl-3-methylaniline | [structure] | — | Bluish green |
| [structure: diethylamino-methyl-benzyl phthalide] | 1,2-dimethylindole | [structure] | 180–182° C. | Blue |
| [structure: dimethylamino-methoxy-benzyl phthalide] | " | [structure] | 191–192° C. | " |
| [structure: diethylamino-ethoxy-benzyl phthalide] | " | [structure] | 215–216° C. | " |

| 3-phenylphthalide derivatives | aniline indole derivatives | resultant compound | m.p. | color |
|---|---|---|---|---|
| " | 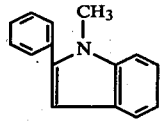 | 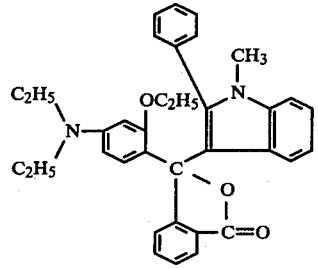 | 108–115° C. | " |
| 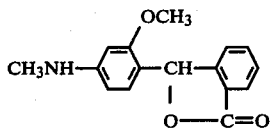 | 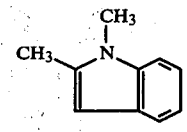 | 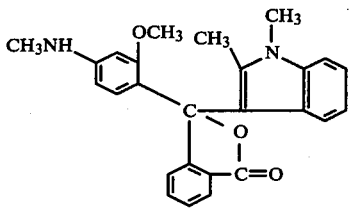 | 200–202° C. | " |
| 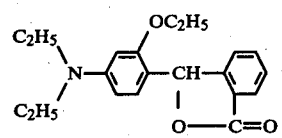 | 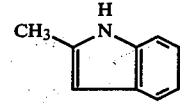 | 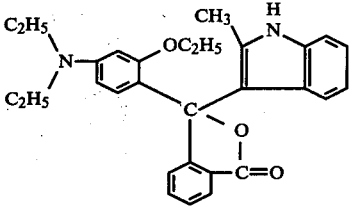 | 223–225° C. | blue |
| 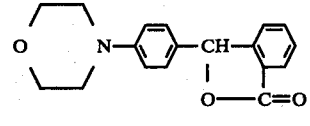 | 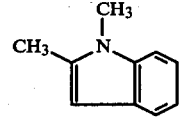 | 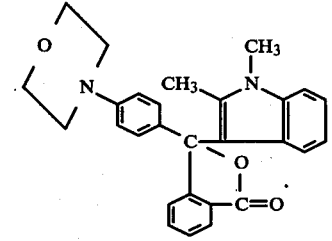 | 238–239° C. | reddish violet |
| 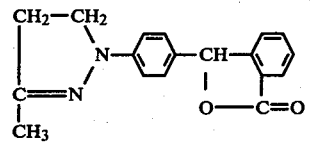 | " | 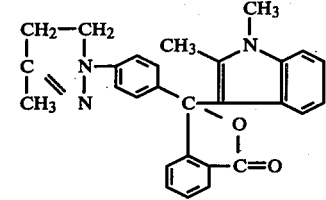 | 242–243° C. | reddish violet |
| 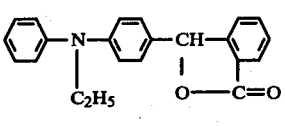 | 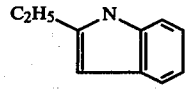 | 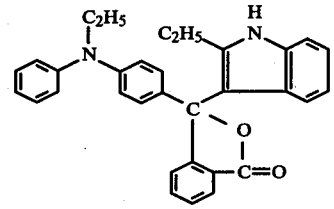 | 95–98° C. | violet |

-continued

| 3-phenylphthalide derivatives | aniline indole derivatives | resultant compound | m.p. | color |
|---|---|---|---|---|
| | | | 102–105° C. | bluish green |
| | | | 125–128° C. | bluish green |
| | | | 263–265° C. | blue black |
| " | | | 235–237° C. | green |
| | | | 220–223° C. | blue |

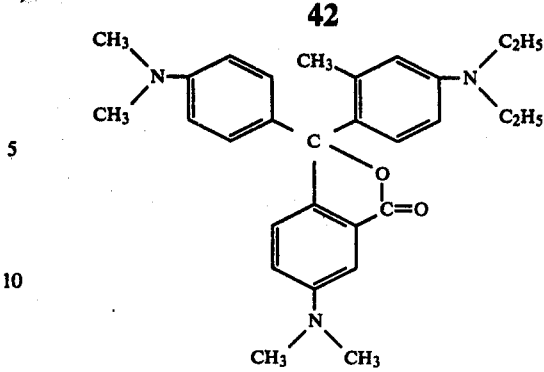
EXAMPLE 22
Example 21 was repeated with use of the various triarylmethane derivatives obtained in Examples 3 to 11 and the various oxidizing agents and solvents as shown in the following table to prepare the various triarylmethane lactone derivatives. The colours which were formed on silica gel are shown in the following table as well.

| triarylmethane derivatives | solvents | oxidizing agents | resultant compounds | m.p. | color |
|---|---|---|---|---|---|
| [structure: 4,4'-bis(dimethylamino)triphenylmethane-2-carboxylic acid] | aqueous solution of caustic soda | KMnO₄ | [structure: lactone form] | 190–191° C. | bluish green |
| [structure: bis(dimethylamino)-methoxy triphenylmethane carboxylic acid derivative] | dilute hydrochloric acid | FeCl₃ | [structure: lactone form] | 208–210° C. | bluish green |

-continued

| triarylmethane derivatives | solvents | oxidizing agents | resultant compounds | m.p. | color |
|---|---|---|---|---|---|
| [structure] | dilute sulfuric acid | $Fe_2(SO_4)_3$ | [structure] | 203–205° C. | violet |
| [structure] | aqueous solution of caustic soda | NaClO | [structure] | 235–236° C. | blue black |

-continued
| triarylmethane derivatives | solvents | oxidizing agents | resultant compounds | m.p. | color |
|---|---|---|---|---|---|
| 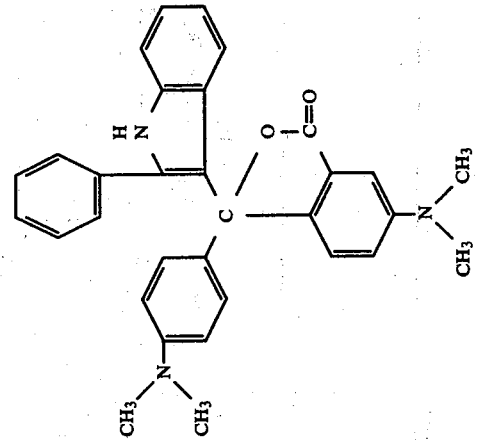 | acetic acid | CH₃COOOH | 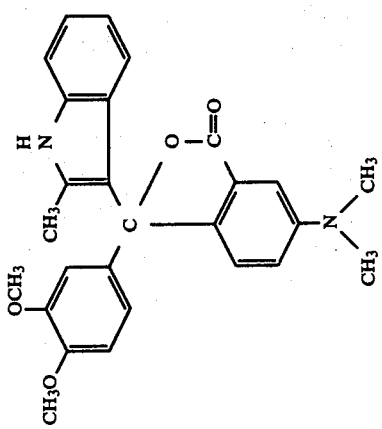 | 244–245° C. | bluish violet |
| 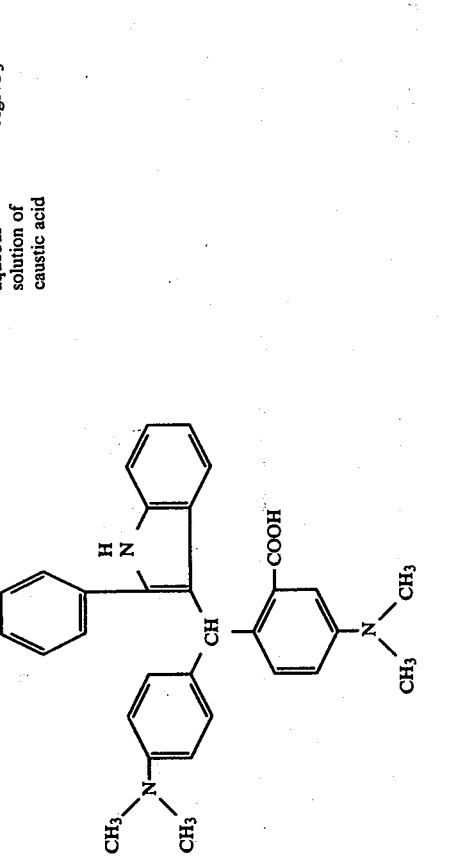 | aqueous solution of caustic acid | AgNO₃ | 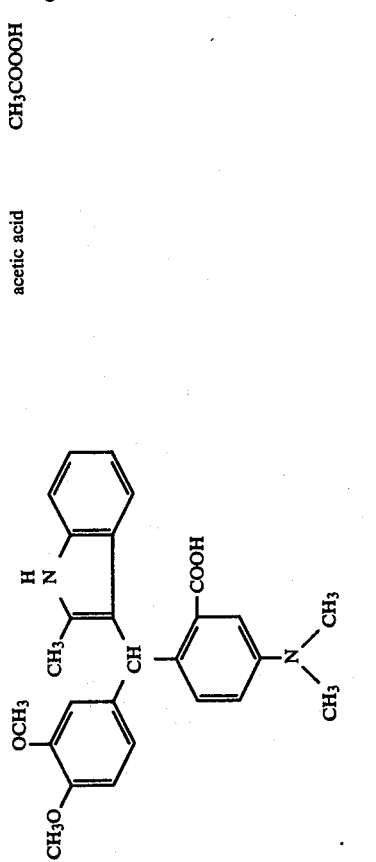 | 252–253° C. | blue |

-continued

| triarylmethane derivatives | solvents | oxidizing agents | resultant compounds | m.p. | color |
|---|---|---|---|---|---|
| (structure) | dilute hydrochloric acid | PbO$_2$ | (structure) | 213–215° C. | bluish violet |
| (structure) | aqueous solution of caustic soda | K$_2$S$_2$O$_8$ | (structure) | 167–168° C. | bluish green |

-continued
| triarylmethane derivatives | solvents | oxidizing agents | resultant compounds | m.p. | color |
|---|---|---|---|---|---|
| 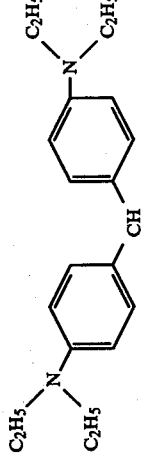 | dilute hydrochloric acid | PbO₂ | 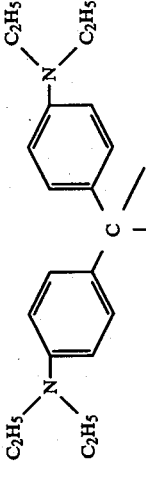 | 172–175° C. | blue |
| 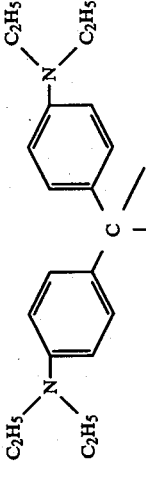 | dilute hydrochloric acid | PbO₂ | 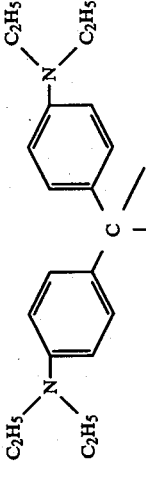 | 80–85° C. | blue |

-continued

| triarylmethane derivatives | solvents | oxidizing agents | resultant compounds | m.p. | color |
|---|---|---|---|---|---|
| [structure with CH, COOH, two N(CH3)2 groups, and CH3-N-CH2-phenyl] | dilute hydrochloric acid | CuCl2 | [corresponding lactone structure] | — | blue |
| [structure with CH, COOH, two N(CH3)2 groups, and CH3-N-(p-tolyl) with CH3] | aqueous solution of caustic soda | Na2S2O8 | [corresponding lactone structure] | — | blue |

-continued

| triarylmethane derivatives | solvents | oxidizing agents | resultant compounds | m.p. | color |
|---|---|---|---|---|---|
| (structure with CH center, two 4-(dimethylamino)phenyl groups, COOH, and 4-piperidinyl phenyl) | aqueous solution of caustic soda | Na₂S₂O₈ | (corresponding triarylmethane dye with C=O lactone, two 4-(dimethylamino)phenyl groups, and piperidinyl-substituted phenyl) | — | blue |
| (structure with CH center, two 4-(dimethylamino)phenyl groups, COOH, Cl, and N(CH₃)₂ substituents) | aqueous solution of caustic soda | Na₂S₂O₈ | (corresponding triarylmethane dye lactone form with Cl and N(CH₃)₂ substituents) | — | blue |

-continued
| triarylmethane derivatives | solvents | oxidizing agents | resultant compounds | m.p. | color |
|---|---|---|---|---|---|
| 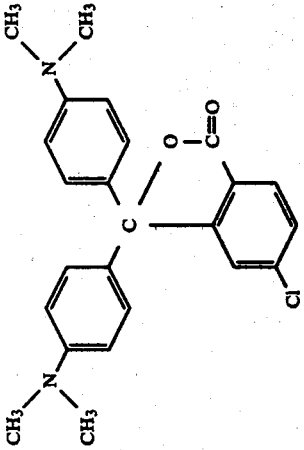 | dilute sulfuric acid | $K_2Cr_2O_7$ | 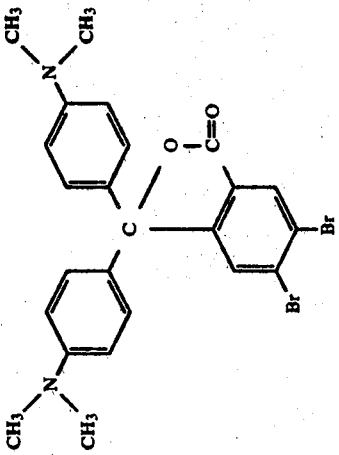 | 186–187° C. | bluish green |
| 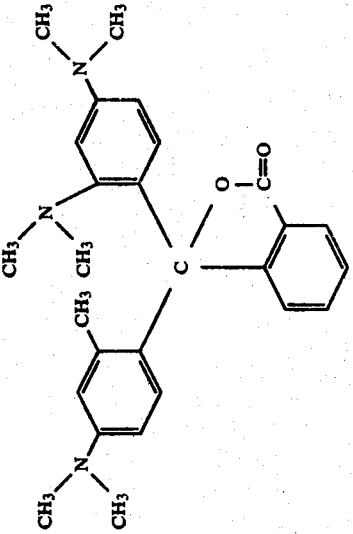 | aqueous solution of caustic soda | $H_2O_2$ | | 218° C. | bluish green |
| 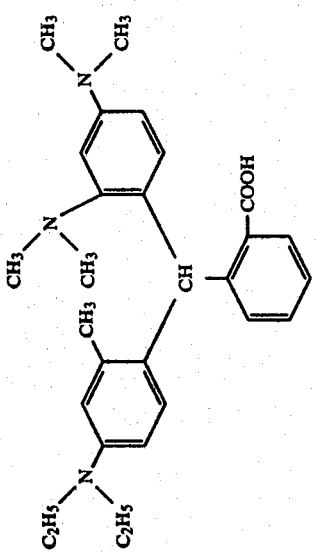 | aqueous solution of caustic soda | $H_2O_2$ | | 204–206° C. | blue black |

-continued
| triarylmethane derivatives | solvents | oxidizing agents | resultant compounds | m.p. | color |
|---|---|---|---|---|---|
| 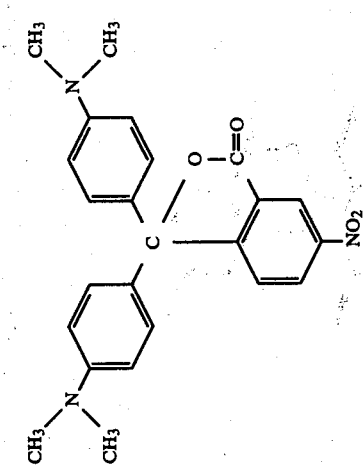 | aqueous solution of caustic soda | $H_2O_2$ | 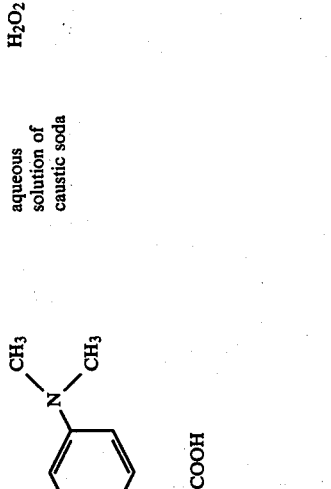 | — | bluish green |
| 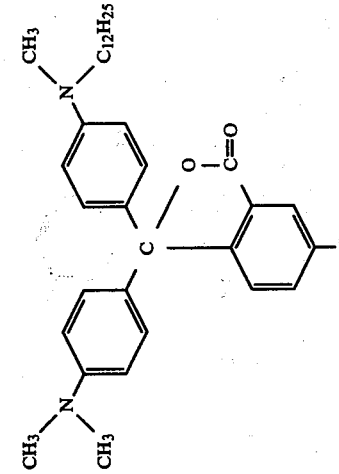 | aqueous solution of caustic soda | $H_2O_2$ | 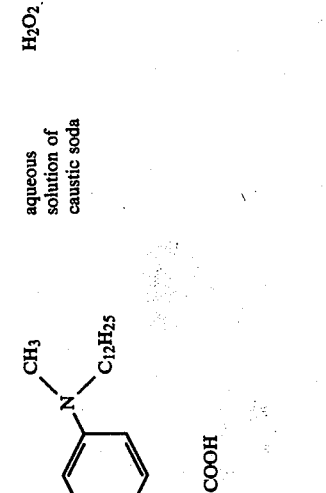 | viscous solid | blue |

-continued

| triarylmethane derivatives | solvents | oxidizing agents | resultant compounds | m.p. | color |
|---|---|---|---|---|---|
| (structure: bis(4-dimethylamino phenyl)-(8-bis(dimethylamino)methyl-naphthyl)-(2-carboxy-4-dimethylamino phenyl)methane leuco form) | aqueous solution of caustic soda | H₂O₂ | (corresponding lactone form) | — | blue black |
| (structure: bis(4-dimethylamino phenyl)-(2-carboxy-4-(N-methyl-N-acetylamino)phenyl)methane leuco form) | ethylene glycol monomethyl ether | chloranil | (corresponding lactone form) | 151–152° C. | bluish green |

-continued

| triarylmethane derivatives | solvents | oxidizing agents | resultant compounds | m.p. | color |
|---|---|---|---|---|---|
| [structure: bis(4-dimethylaminophenyl)(4-methylaminophenyl)methane with COOH, CH group] | ethylene glycol monomethyl ether | chloranil | [structure: corresponding triarylmethane dye with lactone ring] | 183–186° C. | blue |
| [structure: 2-chloro-4-dimethylamino analog with COOH] | aqueous solution of caustic soda | $K_2S_2O_8$ | [structure: corresponding chloro-substituted triarylmethane dye with lactone] | — | blue |

| triarylmethane derivatives | solvents | oxidizing agents | resultant compounds | m.p. | color |
|---|---|---|---|---|---|
| Bis[4-(diethylamino)-2-methoxyphenyl][4-(bis(methyl)amino)phenyl] derivative with COOH and OCH₃, CH₃ substituents (see structure) | aqueous solution of caustic soda | K₂S₂O₈ | Corresponding triarylmethane lactone with OCH₃ and N(C₂H₅)₂, N(CH₃)₂ substituents (see structure) | — | blue |
| Bis-substituted derivative with SCH₃, Cl, COOH and N(CH₃)₂ substituents (see structure) | aqueous solution of caustic soda | K₂S₂O₈ | Corresponding lactone with SCH₃, Cl and N(CH₃)₂ substituents (see structure) | — | blue |

What we claim is:

1. Triarylmethane derivative having the structural formula:

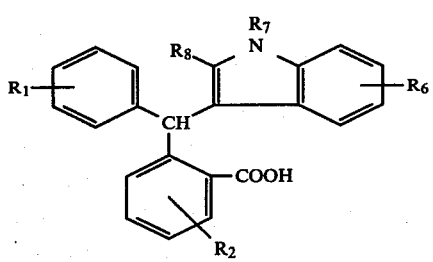

wherein each $R_1$ and $R_2$ represent at least one of hydrogen, halogen, a nitro group, an alkyl group, an amino group, an alkyl-, benzyl-, phenyl-, tolyl-, or pentylene-substituted amino group, a hydroxyl group, an alkyl-substituted hydroxyl group, a thiohydroxyl group or an alkyl-substituted thiohydroxyl group, $R_6$ represents at least one of hydrogen, halogen, lower alkyl group, lower alkoxyl group, amino group, lower alkylamino group, nitro group, phenyl group or phenoxy group, $R_7$ represents hydrogen, an alkyl group, an aralkyl group or a phenyl group, $R_8$ represents an alkyl group or alkyl-, halogen-, or alkoxy-substituted or unsubstituted phenyl group.

2. Triarylmethane derivative as claimed in claim 1 having the structural formula:

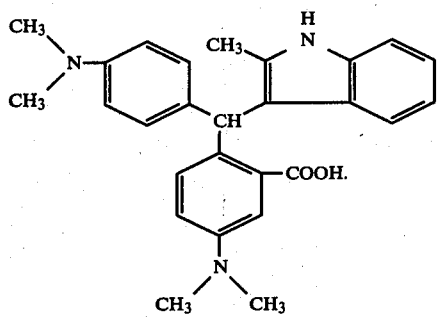

3. Triarylmethane derivative as claimed in claim 1 having the structural formula:

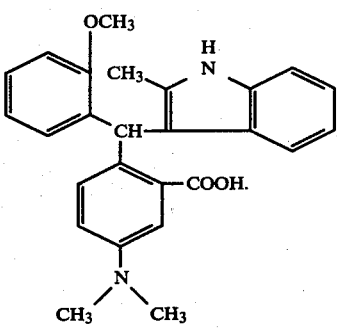

4. Triarylmethane derivative as claimed in claim 1 having the structural formula:

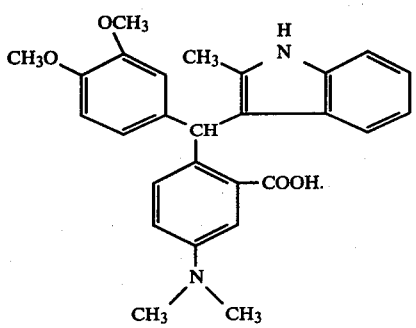

5. Triarylmethane derivative as claimed in claim 1 having the structural formula:

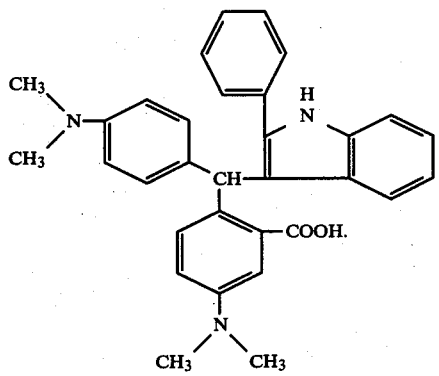

6. Triarylmethane derivative as claimed in claim 1 having the structural formula:

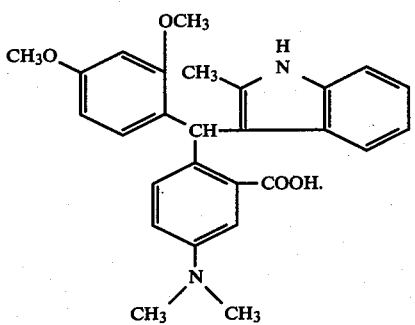

7. Triarylmethane derivative as claimed in claim 1 wherein $R_1$ represents an amino group or an alkyl-, benzyl-, phenyl-, tolyl-, or pentylene-substituted amino group.

8. Triarylamine derivative as claimed in claim 7 wherein $R_2$ represents an alkyl-, benzyl-, phenyl-, tolyl-, or pentylene-substituted amino group and $R_6$ and $R_7$ each represent hydrogen.

* * * * *